United States Patent
Payne et al.

(10) Patent No.: US 6,207,171 B1
(45) Date of Patent: Mar. 27, 2001

(54) POLYPHOSPHAZENE MICROSPHERES

(75) Inventors: Lendon G. Payne, Arlington; Angela L. Woods, West Roxbury, both of MA (US); Sharon A. Jenkins, Bethlehem, NH (US)

(73) Assignee: Avant Immunotherapeutics, Inc., Needham, MA (US)

( * ) Notice: Subject to any disclaimer, the term of this patent is extended or adjusted under 35 U.S.C. 154(b) by 0 days.

(21) Appl. No.: 09/276,024

(22) Filed: Mar. 25, 1999

Related U.S. Application Data

(60) Provisional application No. 60/079,776, filed on Mar. 27, 1998.

(51) Int. Cl.⁷ .................................................. A61K 39/39
(52) U.S. Cl. ............................ 424/280.1; 424/204.1; 424/1.11; 424/209; 435/5; 536/1.11; 514/75; 514/110; 514/114; 514/137
(58) Field of Search ........................... 424/280.1, 204.1, 424/1.11, 209.1; 435/5; 536/1.11; 514/75, 110, 114, 137

(56) References Cited

U.S. PATENT DOCUMENTS

| | | |
|---|---|---|
| 5,494,673 * | 2/1996 | Andrianov et al. ................ 424/280.1 |
| 5,529,777 | 6/1996 | Andrianov et al. ................ 424/184.1 |
| 5,562,909 * | 10/1996 | Allcock et al. ................... 424/280.1 |
| 5,855,895 * | 1/1999 | Andrianov et al. ................ 424/280.1 |

OTHER PUBLICATIONS

O'Hagan, et al., *Vaccine,* vol. 7, pp. 213–216 (Jun. 1989).

O'Hagan, et al., *Vaccine,* vol. 7, pp. 421–424 (Oct. 1989).

Payne et al. 1998, Vaccine, vol. 16, No. 1, pp. 92–98, Jan. 1998.*

Andrianov et al, 1998, Biomaterials, vol. 19, pp. 109–115, Jan. 1998.*

* cited by examiner

*Primary Examiner*—Ali R. Salimi
(74) *Attorney, Agent, or Firm*—Elliot M. Olstein; Raymond J. Lillie

(57) ABSTRACT

A soluble polyphosphazene polyelectrolyte immunoadjuvant is disclosed. In one embodiment, the polymeric adjuvant is poly[di(carboxylatrophenoxy)phosphazene] which is in the form of a microsphere and which is adsorbed with antigen after formation of the microsphere. The immunoadjuvant can be administered intranasally.

5 Claims, 6 Drawing Sheets

POLYPHOSPHAZENE MICROSPHERES

This application claims benefit to U.S. Provisional No. 60/079,776 filed Mar. 27, 1998.

Current research in vaccine development has focused on treatment requiring a single administration, since the major disadvantage of many currently available vaccines is that repeated administrations are required. The ability now exists to provide the controlled release of proteins through microencapsulation of proteins in water soluble polymers thus making single administration vaccines possible. Microencapsulation has been applied to the development of vaccines for administration by both parenteral and mucosal routes. A frequent choice of carrier used in these vaccines is poly (d,1-lactide-co-glycolide) (PLGA), a biodegradable polyester that has a long history of medical use in erodible sutures, bone plates and other temporary prostheses. Adaptation of PLGA for the controlled release of antigen has been described (Eldrige, J. H. et al., *Curr. Top. Microbiol. Immunol.*, 146:59–66 (1989); Eldrige, J. H. et al., *Infect. Immun.*, 59:2978–2986 (1991)). The entrapment of antigens in PLGA microspheres of 1 to 10 microns in diameter has been shown to enhance immune responses. However, the PLGA system requires the use of organic solvents and long preparation times for microencapsulation of antigens, which may adversely affect the immunogenicity of the antigens, particularly labile antigens.

Ionically cross-linkable water soluble polymers, poly[di (carboxylatophenoxy)phosphazene]s (PCPPs) have been developed (Allcock, H. R. and S. Swan, *Macromolecules*, 22:75–79 (1989)). In the soluble state, PCPP has been demonstrated to have adjuvant activity (U.S. Pat. No. 5,494,673) and has enhanced the immunogenicity of various antigens (Payne, L. G. et al., *Vaccine*, 16:92–98(1998)). Generally, the addition of PCPP to antigen preparations has enhanced functional hemagglutination inhibition (HAI) antibody response and has enhanced IgM, IgG, and IgG1 ELISA antibody titers over the levels elicited by vaccine alone. PCPP as an adjuvant has been demonstrated to be as efficient as or to outperform complete Freund's adjuvant. The immunogenicity of antigens as diverse as tetanus toxoid, hepatitis B surface antigen, *Hemophilus influenzae* type b polyribosribotolphosphate, herpes simplex virus type 2 glycoprotein D and HIV env has been dramatically enhanced in the presence of soluble PCPP (Payne, L. G. et al., *Modulation of the Immune Response to Vaccine Antigens*, Lars Haaheim, ed, Geneva (1997); Lu, Y. et al., *J. AIDS Human Retrovirol.*, 12:99–106 (1996)).

Polymeric hydrogel microspheres can be prepared from PCPP which encapsulate antigens and that, throughout their preparation, are exposed only to an aqueous environment (Cohen, S. et al., *J. Am. Chem. Soc.*, 112:78320–7833 (1990); Payne, L. G. et al., *Adv. Exp. Med. Biol.*, McGee, J. R. and J. Mestecky, eds, New York (1994)). In microencapsulation, the antigen is entrapped in the microsphere matrix during the generation of the microspheres. Water soluble PCPP and antigen solution are formulated into hydrogel microspheres by cross-linking carboxyl groups with divalent cations (Payne, 1994). Gelation by ionic crosslinking of the aqueous based polymer solution at room temperature has eliminated long exposure to organic solvents, elevated temperatures and drying required for polymers dissolved in organic solvents, thus maintaining antigenic integrity.

These microspheres are suitable for parenteral or mucosal immunization (Payne, L. G. et al., *Vaccine Design*, Powell, M. F. and M. J. Neuman, eds, New York (1995)). The hydrogel properties of these microspheres allow a sustained antigen release to maximally stimulate the immune response over a long period.

Two methods have been developed to generate PCPP microspheres: a spray method (see U.S. Pat. No. 5,529,777) and an aqueous coacervation method (see U.S. patent application Ser. No. 08/675,713). We have previously demonstrated that antigens encapsulated in ionically-crosslinked PCPP microspheres formed by a spray methodology were able to induce an immune response when administered by a mucosal route. Microencapsulated proteins produced by coacervation methodology eliminates the use of organic solvents and heat used in preparing PLGA microspheres, and avoids the complicated manufacturing equipment and generation of aerosols required for producing spray microspheres.

SUMMARY OF THE INVENTION

It is an object of the present invention to produce an antigen-microsphere formulation by adsorbing the antigen onto preformed microspheres. The present invention describes a polymeric microsphere structure that can efficiently adsorb and/or absorb antigen from a solution. The novel antigen/microsphere formulations provide enhanced immune responses in animals to the antigen. Applicants have found that an immune response against antigen is enhanced by administration of polyphosphazene microspheres in which the antigen is simply absorbed, adsorbed or linked to the surface of the microsphere after production of the microsphere.

μl of microspheres incubated 24 hours with the influenza proteins; Lane 4, 15 μl of microspheres incubated 30 minutes with the influenza proteins; Lane 5, 7.5 μl of microspheres incubated 30 minutes with the influenza proteins.

Figure 5:
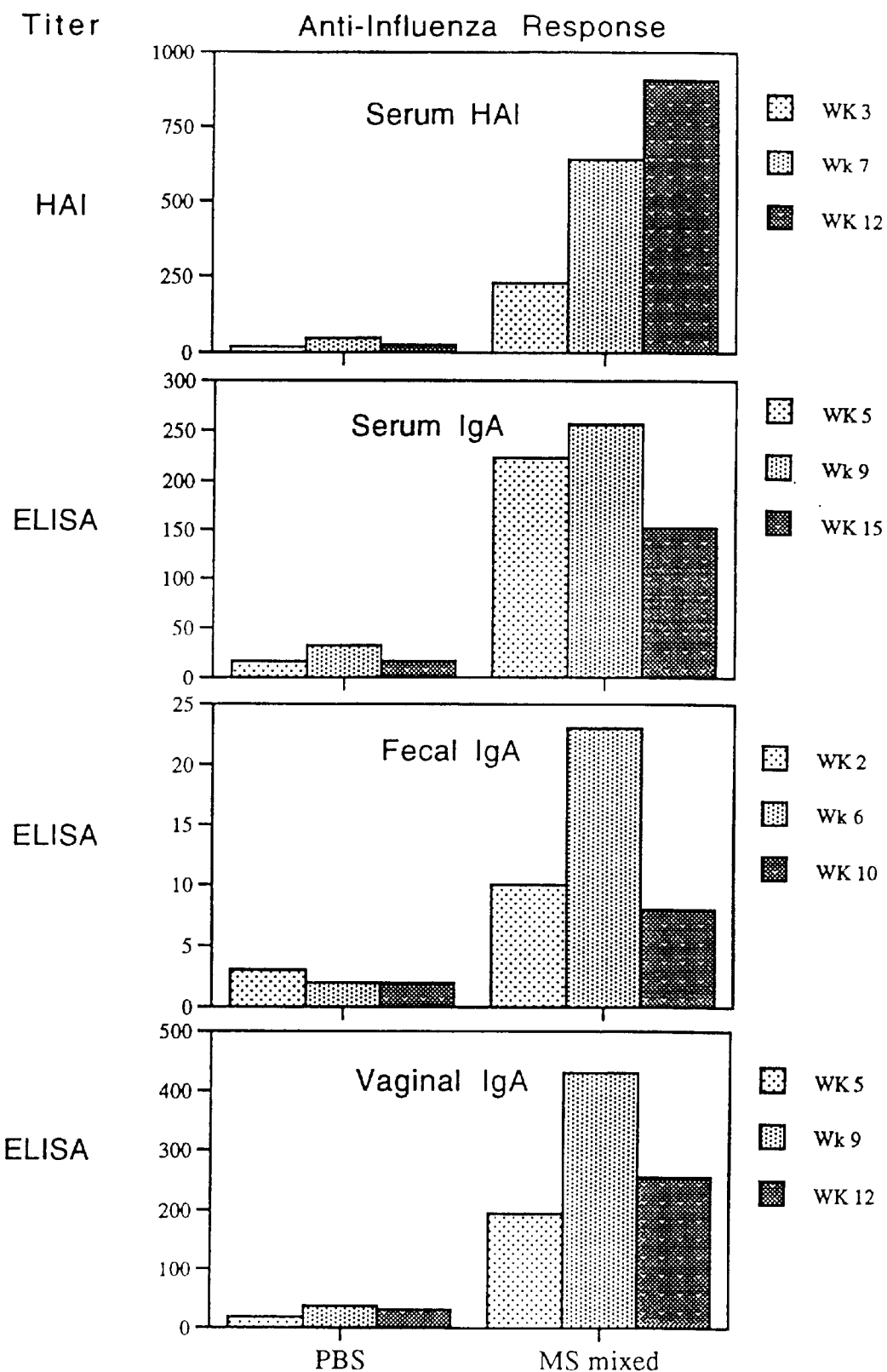

FIG. 5 illustrates ELISA results of samples taken from anesthetized mice administered with influenza antigen mixed with and adsorbed to microspheres (MS) generated by spray methodology. A control group was immunized intranasally with influenza in PBS.

Figure 6:
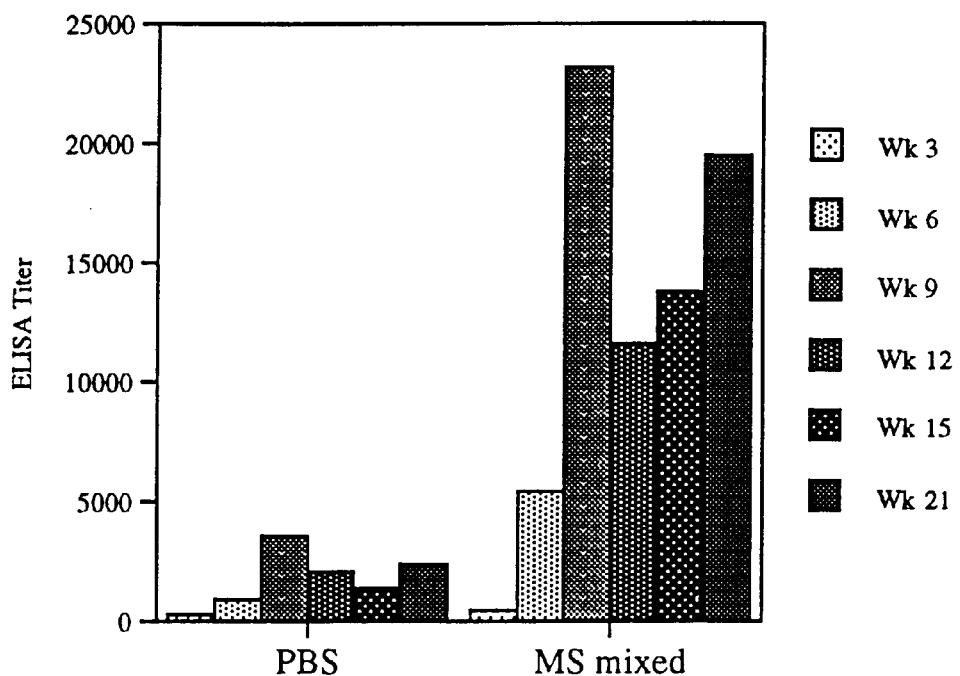

FIG. 6 shows the ELISA results illustrating anti-influenza IgG response of mice to intranasal administration of split X31 influenza mixed with and adsorbed to microspheres prepared by spray methodology.

DETAILED DESCRIPTION OF THE INVENTION

In general, microspheres onto whose surface antigens are adsorbed are formed by covalent or ionic cross-linking of water soluble polymers or polymers that form hydrogels. In the preferred embodiment, the polymers are formed of polyphosphazenes that are ionically cross-linked with divalent cations such as calcium ions to form a water-insoluble hydrogel. More stable microspheres can be formed by further crosslinking the microspheres with a polyelectrolyte such as a polyamino acid.

In the present invention, antigen in solution is mixed with the already formed microspheres and is adsorbed or absorbed to the formed microsphere surface. Applicants have unexpectedly found that an enhanced immune response against an antigen can be obtained when the antigen is simply adsorbed or linked to the microsphere surface. The antigen retains its immunogenic properties and successfully provides an enhanced immune response when administered mucosally.

Polymers useful for making microspheres can be any suitable biocompatible, crosslinkable water-soluble polymer or polymeric hydrogel which can be used to form a microparticle having a diameter of ten microns or less, under gentle conditions. As used herein, a hydrogel is defined as any water-swollen polymer. Water-soluble polymers are those that are at least partially soluble (typically to an extent of at least 0.001% by weight) in water, an aqueous buffered salt solution, or aqueous alcohol solution. Preferred natural water soluble polymers include alginate, gelatin, pectin, and collagen; preferred synthetic water soluble polymers include poly(acrylamide), poly(methacrylamide), poly(vinyl acetate), poly(N-vinyl pyrrolidone), poly(hydroxyethylmethacrylate), poly(ethylene glycol), polyvinylamines, poly(vinylpyridine), phosphazene polyelectrolytes, and poly(vinyl alcohols); preferred polymers forming hydrogels by ionic crosslinking include poly(acrylic acids) or poly(methacrylic acid), sulfonated polystyrene, quaternary salts of either polyamines or poly(vinylpyridine); and mixtures and copolymers of the polymers or monomers thereof. The most preferred polymer is polyphosphazene.

The polymers can be crosslinked either by ionic crosslinking, covalent crosslinking or physical crosslinking to render the water-soluble polymers water-insoluble. Hydrogel is formed by ionic crosslinking of an aqueous based polymer solution at room temperature. The polymers can be crosslinked in an aqueous solution containing multivalent ions of the opposite charge to those of the charged side groups, such as multivalent cations if the polymer has acidic side groups or multivalent anions if the polymer has basic side groups. Preferably, the polymers are cross-linked by di- and trivalent metal ions such as calcium, copper, aluminum, magnesium, strontium, barium, tin, zinc, and iron; or polycations such as poly(amino acid)s, poly(ethyleneimine), poly(vinylamine), poly(vinylpyridine), polysaccharides, and others that can form polyelectrolyte complexes.

The elucidation of a class of ion cross-linkable water soluble polyphosphazenes, described by H. R. Allcock and S. Kwon, *Macromolecules* 22, 75–79 (1989), has made it possible to generate microspheres that throughout preparation are exposed only to an aqueous environment.

Polyphosphazenes are polymers with backbones consisting of alternating phosphorus and nitrogen, separated by alternating single and double bonds. Each phosphorous atom is covalently bonded to two pendant groups ("R"). The repeat unit in polyphosphazenes has the following general formula:

$$-(-\underset{R}{\overset{R}{P}}=N-)_n-$$

wherein n is an integer.

The substituent ("R") can be any of a wide variety of moieties that can vary within the polymer, including but not limited to aliphatic, aryl, aralkyl, alkaryl, carboxylic acid, heteroaromatic, carbohydrates, including glucose, heteroalkyl, halogen, (aliphatic)amino, including alkylamino-, heteroaralkyl, di(aliphatic)amino- including dialkylamino-, arylamino-, diarylamino-, alkylarylamino-,-oxyaryl including but not limited to -oxyphenylCO$_2$H, -oxyphenylSO$_3$H, -oxyphenylhydroxyl and -oxyphenylPO$_3$H; -oxyaliphatic including -oxyalkyl, -oxy(aliphatic)CO$_2$H,-oxy (aliphatic)SO$_3$H, -oxy(aliphatic)PO$_3$H, and -oxy(aliphatic)hydroxyl, including -oxy(alkyl) hydroxyl; -oxyalkaryl, -oxyaralkyl, -thioaryl, -thioaliphatic including -thioalkyl, -thioalkaryl, -thioaralkyl, —NHC(O)O-(aryl or aliphatic), —O—[(CH$_2$)$_x$O]$_y$—CH$_2$)—O—[(CH$_2$)$_x$O]$_y$(CH$_2$)$_x$NH(CH$_2$)$_x$SO$_3$H, and —O—[(CH$_2$)$_x$O]$_y$-(aryl or aliphatic), wherein x is 1–8 and y is an integer of 1 to 20. The groups can be bonded to the phosphorous atom through, for example, an oxygen, sulfur, nitrogen, or carbon atom.

In general, when the polyphosphazene has more than one type of pendant group, the groups will vary randomly throughout the polymer, and the polyphosphazene is thus a random copolymer. Phosphorous can be bound to two like groups, or two different groups. Polyphosphazenes with two or more types of pendant groups can be produced by reacting poly(dichlorophosphazene) with the desired nucleophile or nucleophiles in a desired ratio. The resulting ratio of pendant groups in the polyphosphazene will be determined by a number of factors, including the ratio of starting materials used to produce the polymer, the temperature at which the nucleophilic substitution reaction is carried out, and the solvent system used. While it is very difficult to determine the exact substitution pattern of the groups in the resulting polymer, the ratio of groups in the polymer can be easily determined by one skilled in the art.

Phosphazene polyelectrolytes are defined herein as polyphosphazenes that contain ionized or ionizable pendant groups that render the polyphosphazene anionic, cationic or amphiphilic. The ionic groups can be in the form of a salt, or, alternatively, an acid or base that is or can be at least partially dissociated. Any pharmaceutically acceptable monovalent cation can be used as counterion of the salt, including but not limited to sodium, potassium, and ammonium. The phosphazene polyelectrolytes can also contain non-ionic side groups. The phosphazene polyelectrolyte can be biodegradable or nonbiodegradable under the conditions of use. The ionized or ionizable pendant groups are preferably not susceptible to hydrolysis under the conditions of use.

A preferred phosphazene polyelectrolyte is a polyanion and contains pendant groups that include carboxylic acid, sulfonic acid, hydroxyl, or phosphate moieties. While the acidic groups are usually on nonhydrolyzable pendant groups, they can alternatively, or in combination, also be positioned on hydrolyzable groups. An example of a phosphazene polyelectrolyte having carboxylic acid groups as side chains is shown in the following formula:

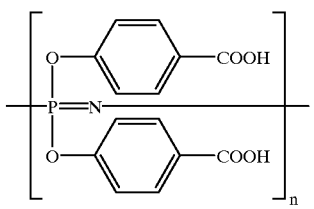

wherein n is an integer, preferably an integer between 10 and 10,000. This polymer has the chemical name poly[di(carboxylatophenoxy)phosphazene] or, alternatively, poly[bis(carboxylatophenoxy)phosphazene] (PCPP).

The term amino acid, as used herein, refers to both natural and synthetic amino acids, and includes, but is not limited to alanyl, valinyl, leucinyl, isoleucinyl, prolinyl, phenylalaninyl, tryptophanyl, methioninyl, glycinyl, serinyl, threoninyl, cysteinyl, tyrosinyl, asparaginyl, glutaminyl, aspartoyl, glutaoyl, lysinyl, argininyl, and histidinyl.

The term amino acid ester refers to the aliphatic, aryl or heteroaromatic carboxylic acid ester of a natural or synthetic amino acid.

The term alkyl, as used herein, refers to a saturated straight, branched, or cyclic hydrocarbon, or a combination thereof, typically of $C_1$ to $C_{20}$, and specifically includes methyl, ethyl, propyl, isopropyl, butyl, isobutyl, t-butyl, pentyl, cyclopentyl, isopentyl, neopentyl, hexyl, isohexyl, cyclohexyl, 3-methylpentyl, 2,2-dimenthylbutyl, 2,3-dimethylbutyl, heptyl, octyl, nonyl, and decyl.

The term (alkyl or dialkyl)amino refers to an amino group that has one or two alkyl substituents, respectively.

The terms alkenyl and alkynyl, as used herein, refers to a $C_2$ to $C_{20}$ straight or branched hydrocarbon with at least one double or triple bond, respectively.

The term aryl, as used herein, refers to phenyl or substituted phenyl, wherein the substituent is halo, alkyl, alkoxy, alkylthio, haloalkyl, hydroxyalkyl, alkoxyalkyl, methylenedioxy, cyano, C(O)(lower alkyl), —$CO_2H$, —$SO_3H$, —$PO_3H$, —$CO_2$alkyl, amide, amino, alkylamino and dialkylamino, and wherein the aryl group can have up to 3 substituents.

The term aliphatic refers to hydrocarbon, typically of $C_1$ to $C_{20}$, that can contain one or a combination of alkyl, alkenyl, or alkynyl moieties, and which can be straight, branched, or cyclic, or a combination thereof.

The term halo, as used herein, includes fluoro, chloro, bromo, and iodo.

The term aralkyl refers to an aryl group with an alkyl substituent.

The term alkaryl refers to an alkyl group that has an aryl substituent, including benzyl, substituted benzyl, phenethyl or substituted phenethyl, wherein the substituents are as defined above for aryl groups.

The term heteroaryl or heteroaromatic, as used herein, refers to an aromatic moiety that includes at least one sulfur, oxygen, or nitrogen in the aromatic ring, and that can be optionally substituted as described above for aryl groups. Nonlimiting examples are furyl, pyridyl, pyrimidyl, thienyl, isothiazolyl, imidazolyl, tetrazolyl, pyrazinyl, benzofuranyl, benzothiophenyl, quinolyl, isoquinolyl, benzothienyl, isobenzofuryl, pyrazolyl, indolyl, isoindolyl, benzimidazolyl, purinyl, carbozolyl, oxazolyl, thiazolyl, isothiazolyl, 1,2,4-thiadiazolyl, isooxazolyl, pyrrolyl, pyrazolyl, quinazolinyl, pyridazinyl, pyrazinyl, cinnolinyl, phthalazinyl, quinoxalinyl, xanthinyl, hypoxanthinyl, pteridinyl, 5-azacytidinyl, 5-azauracilyl, triazolopyridinyl, imidazolopyridinyl, pyrrolopyrimidinyl, and pyrazolopyrimidinyl.

The term "pharmaceutically acceptable ion" refers to an organic or inorganic moiety that carries a charge and that can be administered as a counterion in a phosphazene polyelectrolyte.

The term heteroalkyl, as used herein, refers to an alkyl group that includes a heteroatom such as oxygen, sulfur, or nitrogen (with valence completed by hydrogen or oxygen) in the carbon chain or terminating the carbon chain.

The terms poly[(carboxylatophenoxy)(glycinato) phosphazene], poly[di(carboxylatophenoxyphosphazene-co-di(glycinato)phosphazene-co-(carboxylatophenoxy) (glycinato)phosphazene] and poly[di(carboxylatophenoxy) phosphazene-co-di(glycinato)phosphazene] as used herein refer to the same polymer.

The polyphosphazene preferably contains charged side groups, either in the form of an acid or base that is in equilibrium with its counter ion, or in the form of an ionic salt thereof.

The phosphazene polyelectrolyte is preferably biodegradable. The term biodegradable, as used herein, means a polymer that degrades within a period that is acceptable in the desired application, typically less than about five years and most preferably less than about one year, once exposed to a physiological solution of pH 6–8 at a temperature of approximately 25° C.–37° C. The polymer preferably exhibits minimal toxicity when administered to animals, including humans.

Polyphosphazenes, including phosphazene polyelectrolytes, can be prepared by a macromolecular nucleophilic substitution reaction of poly(dichloro phosphazene) with a wide range of chemical reagents or mixture of reagents in accordance with methods known to those skilled in the art. Preferably, the phosphazene polyelectrolytes are made by reacting the poly(dichloro phosphazene) with an appropriate nucleophile or nucleophiles that displace chlorine. Desired proportions of hydrolyzable to non-hydrolyzable side chains in the polymer can be obtained by adjusting the quantity of the corresponding nucleophiles that are reacted with poly (dichlorophosphazene) and the reaction conditions as necessary. Preferred polyphosphazenes have a molecular weight of over 1,000, more preferably from about 500,000 to about 1,500,000.

Poly[di(carboxylatophenoxy)phosphazene] (PCPP) solutions can be prepared by dissolving the appropriate amount of PCPP in PBS pH 7.4 while shaking at 55° C.

The microspheres can be prepared by spray methodology as described in U.S. Pat. No. 5,529,777. Using a syringe pump at a speed of 150 µl/minute, the poly[di (carboxylatophenoxy)phosphazene] (PCPP) polymer solution (prepared as described above) was pumped into a Sonimist (Medisonic, Inc., Farmingdale, N.Y.) ultrasonic nozzle equipped with an 18 gauge blunt-end needle. The needle enabled the solution to be delivered directly to the point of atomization in the nozzle. The polymer solution was then forced through a 0.3 mm orifice in the nozzle under approximately 35 pounds per square inch of air pressure. The PCPP microdroplets were cross-linked when they impacted a 7.5% $CaCl_2$ bath at a distance 60 cm from the nozzle. The microspheres were then quickly transferred to a centrifuge tube and rocked gently for approximately 30 minutes to complete the cross-linking process and to avoid microsphere settling and aggregation. The microspheres were collected by centrifugation at 4° C., 2800 rpm for 15 minutes; the supernatant was discarded, the pellet was washed once and resuspended in sterile deionized water or a low $CaCl_2$ concentration, preferably from about 1–7.5%. The microspheres were stored at 4° C. until analysis or further use.

Alternatively, the microspheres can be prepared by coacervation as described in U.S. Ser. No. 08/675,713. Aqueous poly[di(carboxylatophenoxy)phosphazene] (PCPP) solutions in the range of concentration 0.01%–1.11% were prepared by dissolving the polymer in PBS pH 7.4. The polymer solutions were mixed with sodium chloride solutions (2–30%) in the ratio of 0.4 ml:0.74 ml and agitated by shaking. The solutions or dispersions were examined in the microscope to determine the presence of coacervate droplets or precipitate. The concentration of NaCl in the mixture was plotted against the polymer concentration to establish at which concentration of NaCl and PCPP microspheres were formed.

Ionically cross-linked microspheres of PCPP were prepared by mixing 4 ml of 0.2% solution of PCPP (molecular weight $1.1 \times 10^6$ g/mol) in PBS and 7.4 ml of 6.2% sodium chloride solution in water. The mixture was shaken and incubated at room temperature or until coacervate droplets with a mean size of approximately 4–6 µm were formed, for approximately 6 minutes. The obtained coacervate dispersion was poured into 800 ml of 8.8% calcium chloride solution in water and the suspension was stirred using a magnetic stirrer for 20 minutes. The microspheres were isolated by centrifugation (3000 rpm, 10 minutes), washed with deionized water, collected by centrifugation and stored at 4° C. until further use.

The size of PCPP microspheres was measured utilizing a Coulter LS100 Particle sizer. Size was reported as the percent of the total microsphere preparation having a diameter of between 1–10 µm.

Microspheres were stable for at least 14 days stored at 4° C. in sterile deionized water. Standard buffers such as PBS cannot be used because the replacement of calcium ions with sodium leads to liquification of the matrix.

As used herein, the term "microsphere" encompasses microparticles, empty particles, and microcapsules unless otherwise stated. In general, those microspheres which are useful will have a particle diameter of between one and 200 microns, preferably between one and 15 microns for oral administration, and preferably between one and 100 microns for injection, although the limiting factor for injection is the needle size. For intranasal administration, the particle diameter is preferably between 1 and 15 microns.

Antigen may be derived from a cell, bacterium, virus particle, or a portion thereof. The antigen may be a protein, peptide, polysaccharide, glycoprotein, glycolipid, nucleic acid, or a combination thereof, which elicits an immune response in an animal, including mammals, birds, and fish. The immune response may be a humoral immune response or a cell-mediated immune response. In the event the material to which the immune response is to be directed is poorly antigenic, it may be conjugated to a carrier such as albumin or to a hapten, using standard covalent binding techniques, for example, with one of the several commercially available reagent kits. In some embodiments it may be desirable to include an additional adjuvant with the antigen.

Examples of preferred antigens include viral proteins such as influenza proteins, human immunodeficiency virus HIV proteins, *Haemophilus influenza* proteins, hepatitis B proteins, and bacterial proteins and lipopolysaccharides such as gram negative bacterial cell walls and *Neisseria gonorrhea* proteins.

In a preferred embodiment of the present invention, tetanus toxoid (TT) (Connaught Laboratories) and split influenza virus X-31 (H3N2) (Spafas, Inc.) were used as antigens. The virus had been grown in the allantoic cavities of embryonated chicken eggs according to standard methods. The virus was purified from the allantoic fluid by sucrose gradient ultracentrifugation and quantitated by protein and hemagglutination assays. Split influenza was prepared by solubilizing virus with 0.25% Tween 80 for 30 minutes at 25° C. Thereafter, an equal volume of diethyl ether was added and the solution was gently agitated for 30 minutes at 25° C. Phase separation was achieved by centrifugation at 1500 rpm for ten minutes. The lower phase was collected and residual ether was allowed to evaporate. The split influenza preparation was quantitated by SDS-PAGE and Bio-Rad protein assay.

To prepare an immunogenic composition, the microspheres prepared either by spray methodology or aqueous coacervation methodology are mixed/incubated together with antigen, preferably at room temperature. Incubation/mixing can be for about 30 minutes to about 24 hours to obtain optimal adsorption of the antigen to the microspheres and for optimal immune responses from the resulting immunogenic composition.

Hydrogel microspheres adsorbed with antigen can be administered mucosally or parenterally. Nonlimiting examples of routes of delivery to mucosal surfaces are intranasal (or generally, the nasal associated lymphoid tissue), respiratory, vaginal, and rectal. Nonlimiting examples of parenteral delivery include intradermal, subcutaneous, and intramuscular.

Dosage is determined by antigen loading and by standard techniques for determining dosage and schedules for administration for each antigen, based on titer of antibody elicited by the microsphere-antigen administration, as demonstrated by the examples.

Ethidium bromide was used to track the actual route of dispersion of the administered immunogenic compositions. Results showed that administration of the antigen/microsphere formulation of the present invention via either intranasal or lung tissue immunization routes produced effective increases in desired immune responses compared to controls.

The following are non-limiting examples illustrating the invention described herein. Unless indicated otherwise, the materials and reagents used in the examples are readily available from commercial vendors known to those in the art.

EXAMPLES

Example 1

Immunization. Prepared microspheres were mixed with tetanus toxoid or influenza antigens using the conditions as described below. Female 7–8 week old BALB/c mice (Taconic Germantown, N.Y.) were randomized into groups and immunized with or without anesthesia by intranasal instillation with 10 μl or 50 μl of the antigen formulations. Mice in the anesthetized groups were treated with Metofane (Malinckrodt Veterinary, Mundelein, Ill.) to induce a level 2 state that lasted about 2–3 minutes.

Example 2

Sample collection. Blood samples were taken from the retroorbital sinus of $CO_2$ anesthetized mice. The blood was centrifuged for 10 minutes at 14,000 rpm and sera collected. IgA is very sensitive to freeze-thaw as well as storage at 4° C. so the sera were analyzed for IgA within 24 hours. Sera were stored at −20 ° C. until analyzed for IgM and IgG. Vaginal secretions were collected from $CO_2$ anesthetized mice by washing the vaginal mucosa with 50 μl of sterile PBS. The samples were stored for no longer than 24 hours at 4° C. before being analyzed. Fecal samples were collected from individual mice. Samples were prepared by dissolution in PBS/0.1% sodium azide (Sigma) to a final concentration of 200 mg per ml. Samples were vortexed for 15 minutes and then centrifuged for 15 minutes at 14,000 rpm. Supernatants were collected and stored at 4° C. for no longer than 24 hours before being analyzed.

Example 3

Immune response assays. Tetanus toxoid and influenza specific IgG antibodies in mouse serum, vaginal washes and fecal samples were determined by ELISA in 96-well microtiter plates (Nunc) coated with 1 μg/ml influenza infected MDCK cell lysate or 10 μg per ml of purified influenza virus in sodium carbonate buffer pH 9.6. Sites available for non-specific binding of protein after coating and washing were blocked by adding 2.5% BSA (Sigma, St. Louis, Mo.) in PBS solution. After blocking and washing, twofold serial dilutions of each sample in 1% BSA/PBS were added to the wells and incubated at 37° C. for 1 hour. Unbound sample was washed away and horseradish peroxidase-labelled goat anti-mouse IgG (Sigma, St. Louis, Mo.) was added at a 1:5000 dilution and incubated at 37° C. for one hour. Unbound conjugate was washed away and antibody was detected by adding the substrate o-phenylenediamine dihydrochloride (Sigma). The reaction was stopped after 15 minutes for the tetanus toxoid ELISA and 30 minutes for the influenza ELISA by the addition of 2M $H_2SO_4$ and the absorbance read at 490 nm. The endpoint titers are the reciprocal of the greatest sample producing a signal two-fold greater than that of an antibody negative sample at the same dilution. Negative sera, vaginal washes and fecal samples were used as controls for their respective analyses. Positive controls of known IgG titer were included on all plates. The controls had to fall within two-fold of the expected titer (two-fold below or two-fold above) on all plates or the assay was repeated.

The Ig classes of the ELISA reactive tetanus toxoid and influenza specific antibodies in sera, vaginal washes and fecal samples were determined by detection of murine antibodies bound to the antigens. Horseradish peroxidase labelled goat anti-mouse antibody specific for mouse IgM and IgA (Sigma) was reacted with mouse antibodies bound to the antigen in the ELISA plates. The positive control on the IgM specific ELISA plates was a sample of known IgM titer. The control on the IgA specific ELISA plates was a sample of known IgG titer. Since IgA is known to be unstable under all storage conditions, an IgG positive control was a more reliable control to ensure that the antigen coating on each plate was accurate and that the assay had been technically successful.

Statistical analysis. All antibody titers were expressed as geometric mean titers (GMT). Data were statistically analyzed by Student's t-test of unpaired samples using a Statistica/Mac software (StatSoft, Inc., Tulsa, Okla.). Unless otherwise stated, there were five to eight mice per group in all experiments. Probability values of <0.05 were considered to be significant.

Example 4

The Effect of Anesthesia and Volume on PCPP Distribution in Airways

The depth of penetration of the administered material into the respiratory tree (nasal, bronchial and lung) was determined by tracking the fluorescent dye ethidium bromide, which binds very strongly to PCPP and allows the detection of PCPP in the airways of a mouse (Table 1). Anesthetized and unanesthetized mice were instilled with 50 μg PCPP in 50 μl or 10 μl volumes of a PCPP solution containing ethidium bromide. Unanesthetized mice receiving a 50 μl volume were observed to be actively swallowing during the administration procedure. At 30 minutes post-treatment, the mice were euthanized with $CO_2$, the head sagittaly partitioned and the lumena of the trachae and major bronchi exposed by free dissection. The presence of PCPP on mucosal surfaces was detected by a bright fluorescence under a UV lamp. The ethidium bromide/PCPP material was detected in the nasal cavities of unanesthetized mice regardless of whether the administration volume was 50 μl or 10 μl, indicating true intranasal immunizations. Fluorescence was detected exclusively in the nasal cavities of anesthetized mice inoculated with 10 μl, whereas a 50 μl volume in anesthetized mice was widely dispersed in the airways of the lungs, which indicated 50 μl was a lung tissue immunization.

TABLE 1

ETHIDIUM BROMIDE EXPERIMENT

| ANESTHESIA | VOLUME | DISTRIBUTION |
|---|---|---|
| No | 50 μl | nasal tissue |
| No | 10 μl | nasal tissue |
| Yes | 50 μl | nasal tissue, trachea, lungs |
| Yes | 10 μl | nasal tissue |

Although unknown quantities of an intranasally administered 50 μl volume were swallowed by unanesthetized mice, we do not believe that the swallowed material contributed to the immunization of the animals. Previous experiments showed no immune response in mice administered via pipette feeding or intragastric gavage with preparations that provided an immune response when administered intranasally.

Example 5

Figure 1:
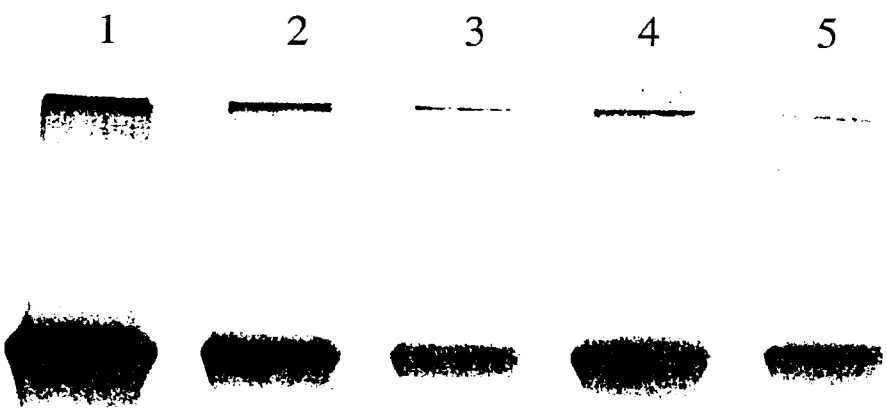
FIG. 1 illustrates PAGE analysis of proteins adsorbed to preformed PCPP microspheres. Tetanus toxoid protein was mixed with preformed PCPP microspheres, incubated, washed, and resuspended as described in Example 8. The protein/microsphere preparation was dissociated in sample buffer and analyzed on a 7.8% SDS polyacrylamide gel and stained with Coomassie blue. The lanes are as follows: Lane 1, starting tetanus toxoid protein; Lane 2, 15 µl of microspheres incubated 24 hours with the tetanus toxoid protein; Lane 3, 7.5 µl of microspheres incubated 24 hours with the tetanus toxoid protein; Lane 4, 15 µl of microspheres incubated 30 minutes with the tetanus toxoid protein; Lane 5, 7.5 µl of microspheres incubated 30 minutes with the tetanus toxoid protein.

Tetanus Toxoid Adsorbed to PCPP Preformed Microspheres $1 \times 10^8$ microspheres generated by coacervation were sedimented by centrifugation (2600 rpm). The microspheres were resuspended in 200 μl volume of PBS containing 500 μg of tetanus toxoid antigen and incubated at room temperature. After incubation, the supernatant was saved for analysis. The microsphere sediment was washed with one ml of water (about 200 times the microsphere pellet volume), sedimented by centrifugation and the supernatant and microsphere pellet analyzed separately. The first and second supernatants were analyzed for protein content by protein assay based on the Bradford method (BioRad Laboratories, Hercules, Calif.). The protein analysis showed that a 30 minute incubation of the antigen/microsphere mixture resulted in the recovery of 20% of the protein in the combined supernatants, therefore 80% of the tetanus toxoid antigen was adsorbed to the microspheres. Samples taken at 24 hours showed between 70–88% adsorption of antigen to the preformed microspheres. The microsphere pellet was resuspended in 500 $\mu l$ of buffer and analyzed by polyacrylamide gel electrophoresis (FIG. 1). Coomassie brilliant blue stained gel patterns of 30 minute and 24 hour incubations of the antigen/microsphere mixture showed equivalent adsorption of the tetanus toxoid protein to microsphere at both times. Furthermore, the pattern of the microsphere adsorbed proteins was indistinguishable qualitatively from the pattern of the starting tetanus toxoid protein pattern.

Example 6

Intranasal Administration of Tetanus Toxoid Microsphere Formulations

Figure 2:
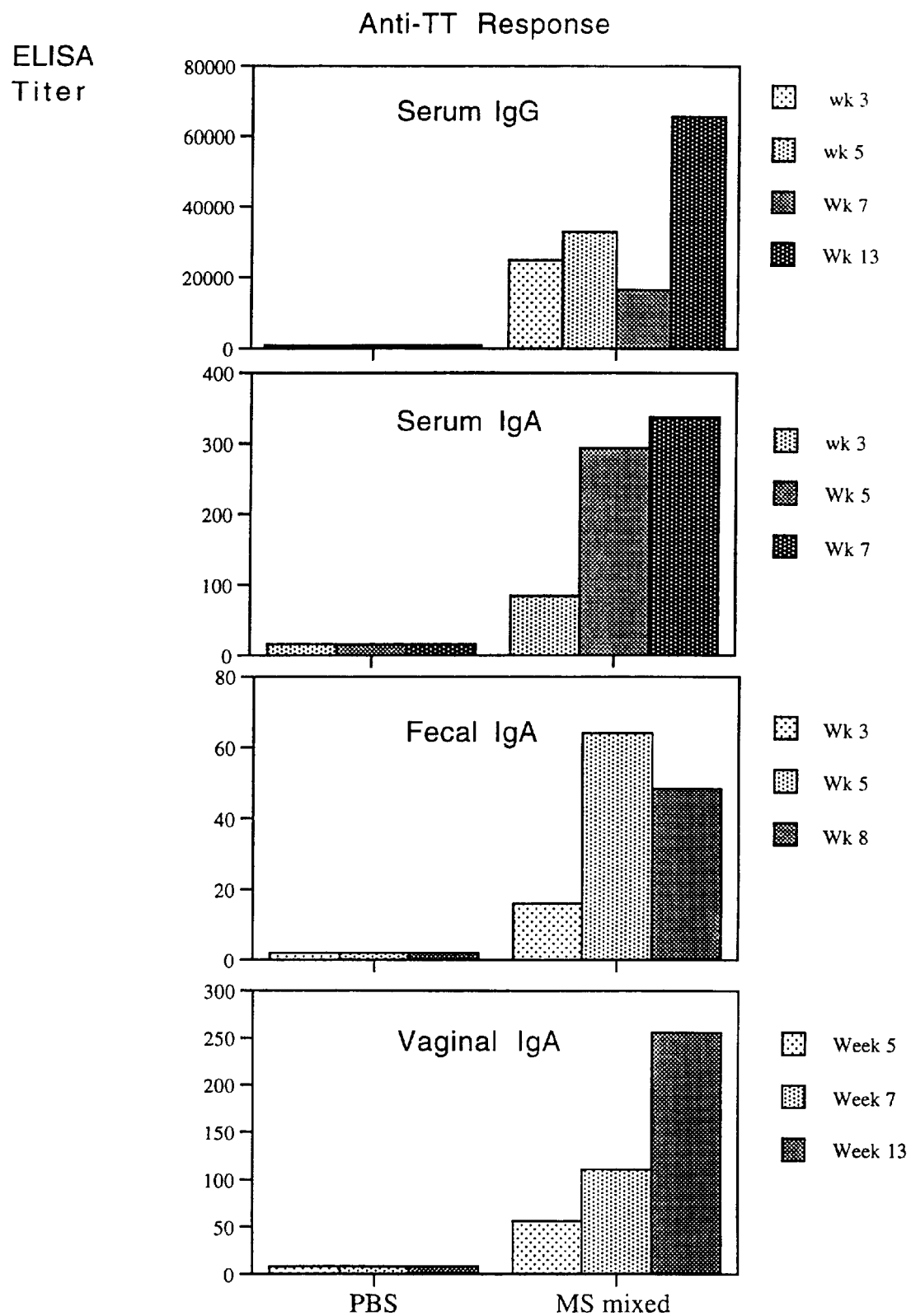
FIG. 2 illustrates the ELISA results of samples taken from anesthetized mice administered intranasally with tetanus toxoid antigen (TT) mixed with and adsorbed to microspheres (MS) generated by spray methodology. A control group was immunized intranasally with 50 µg tetanus toxoid in phosphate buffered saline (PBS).
Figure 3:
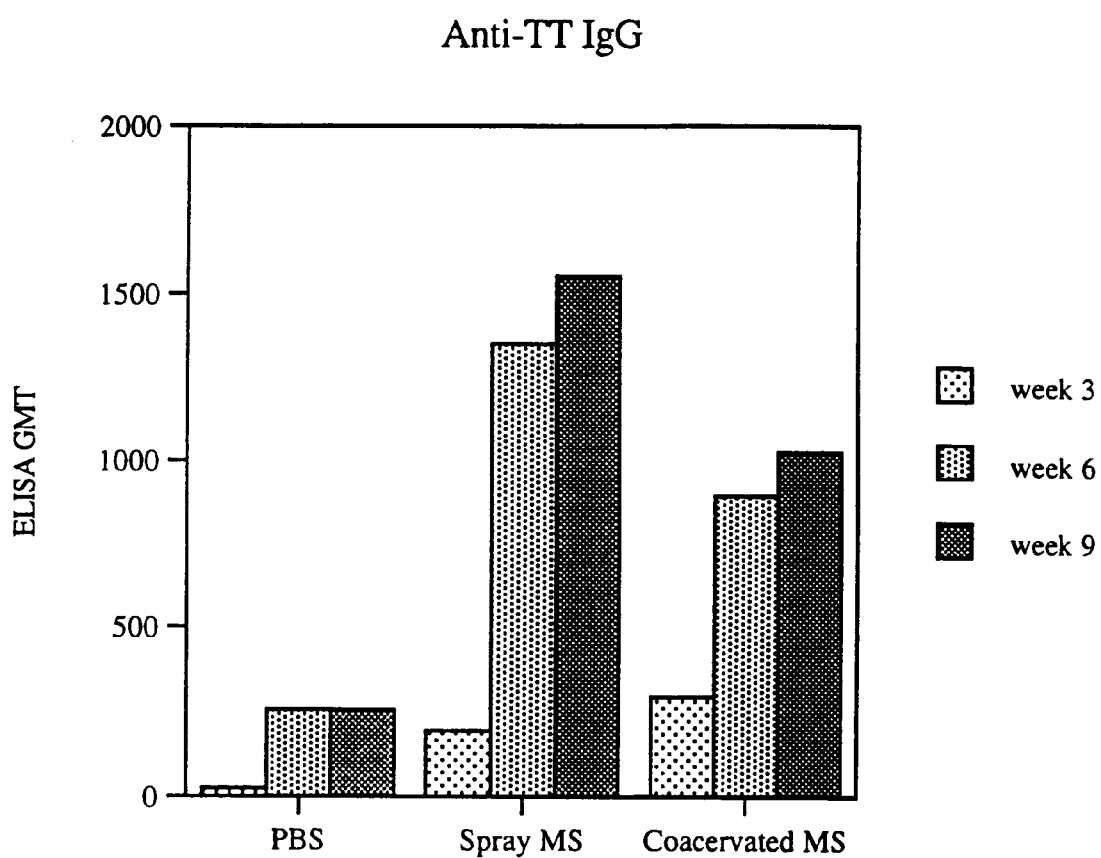
FIG. 3 shows the geometric mean titers (GMT) ELISA results illustrating the anti tetanus toxoid (anti TT)-IgG response of mice to intranasal administration of tetanus toxoid mixed with and adsorbed to microspheres prepared either by spray or coacervation methodologies.
Figure 4:
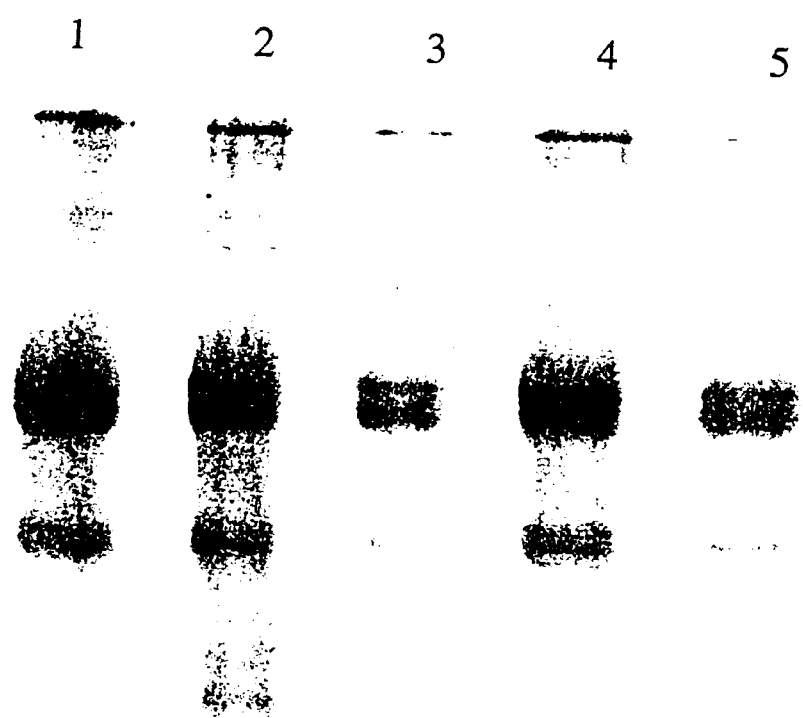
FIG. 4 illustrates PAGE analysis of proteins adsorbed to preformed PCPP microspheres. Split influenza proteins were mixed with PCPP microspheres, incubated, washed and resuspended as described in Example 11. The protein microsphere preparation was dissociated with sample buffer and analyzed on a 7.8% SDS polyacrylamide gel and stained with Coomassie blue. The lanes are as follows: Lane 1, starting influenza proteins; Lane 2, 15 µl of microspheres incubated 24 hours with the influenza proteins; Lane 3, 7.5

Anesthetized mice were immunized intranasally with 50 $\mu g$ of tetanus toxoid (FIG. 2) in PBS or tetanus toxoid mixed with $2\times10^7$ preformed empty PCPP microspheres 30 minutes before immunization. The microspheres were generated by atomization spray methodology. The administration volume was 50 $\mu l$. The serum IgG, serum IgA and secretory IgA (vaginal and fecal) responses were assayed at the indicated time points post-immunization.

Mice immunized with tetanus toxoid mixed with empty PCPP microspheres 30 minutes prior to immunization generated serum IgG, serum IgA, fecal IgA and vaginal IgA titers that were significantly enhanced compared to the PBS tetanus toxoid formulation. The microsphere formulation induced the following increases over the PBS formulation: serum IgG, 21–84 fold; serum IgA, 5–21 fold; fecal IgA, 8–24 fold; vaginal IgA, 7–32 fold.

Example 7

Comparison of Microspheres Generated by the Spray and Coacervation Methods

Microspheres generated by the spray atomization and coacervation methods were compared for their capacity to induce an immune response to antigens that were simply mixed and adsorbed to the preformed microsphere preparations. Tetanus toxoid antigen was mixed with microspheres prepared by either spray atomization or coacervation and the antigen/microsphere mixture was incubated for 30 minutes. 15 $\mu l$ volumes containing 18.75 $\mu g$ of tetanus toxoid and $2\times10^7$ microspheres (MS) were intranasally administered to unanesthetized mice. FIG. 3 shows the immune responses to these two microsphere formulations compared to a control antigen formulation containing only 18.75 $\mu g$ of tetanus toxoid in 15 $\mu l$ of PBS administered intranasally. A detectable ELISA IgG response was observed at 3 weeks for both microsphere formulations, whereas significant antibody formation was not observed at this time point for the PBS formulation. By 9 weeks post-immunization, the tetanus toxoid antibody titers for the spray and coacervation formulations were approximately 6 fold and 4 fold higher, respectively, than the PBS formulation.

The data from the tetanus toxoid immunization experiments demonstrated that intranasal administration of 50 $\mu l$ volumes to anesthetized mice was essentially a lung tissue immunization that induced very high IgG and secretory IgA antibody titers. Intranasal administration of 10 $\mu l$ volumes to anesthetized mice, on the other hand, was a true intranasal immunization that induced much lower IgG than the 50 $\mu l$ volumes but no significant secretory IgA antibody titers were induced. Intranasal administration of 50 $\mu l$ and 10 $\mu l$ volumes to unanesthetized mice was a true intranasal immunization that elicited similar IgG antibody titers although these titers were lower than the titers induced by the 50 $\mu l$ volumes in anesthetized mice. The unanesthetized mice did not respond with significant secretory IgA antibody titers.

Example 8

Influenza Antigens Mixed with PCPP Microspheres Are Adsorbed $1\times10^8$ microspheres generated by coacervation were sedimented by centrifugation (2600 rpm). The prepared microspheres were resuspended in 250 $\mu l$ volume of PBS containing 250 $\mu g$ of split influenza antigens and incubated at room temperature. After incubation, the supernatant was saved for analysis. The antigen adsorbed microsphere sediment was washed with one ml of water (about 200 times the microsphere pellet volume), sedimented by centrifugation and the supernatant and microsphere pellet were separated and analyzed. The first and second supernatants were analyzed for protein content with a BioRad kit. The protein analysis showed that a 30 minute incubation of the antigen/microsphere mixture resulted in the recovery of 10% of the protein in the combined supernatants, therefore, 90% of the influenza antigen was adsorbed to the microspheres. Samples taken at 24 hours showed between 84–91% adsorption. The microsphere pellet was resuspended in 250 $\mu l$ of buffer and analyzed by polyacrylamide gel electrophoresis (FIG. 4). Coomassie brilliant blue stained gel patterns showed no difference in the amount of antigen adsorbed to the microspheres after 30 minute and 24 hour incubations of the antigen/microsphere mixture. All of the detectable influenza protein species were adsorbed to the microspheres resulting in a protein pattern that was indistinguishable qualitatively and quantitatively from the pattern of the starting split influenza protein pattern. Thus, there is no preferential adsorption onto already prepared microspheres of one protein species over another.

Example 9

Intranasal Administration of Influenza Microsphere Formulations

Anesthetized mice were immunized intranasally with 50 $\mu g$ split X31 influenza virus (FIG. 5) in PBS or influenza virus mixed 30 minutes before immunization with already prepared empty PCPP microspheres. The microspheres were generated by the atomization spray methodology. The administration volume was 50 $\mu l$. The serum HAI, serum IgA and secretory IgA (vaginal and fecal) responses were assayed at the indicated time points post-immunization.

Intranasal administration of anesthetized mice with influenza mixed with empty microspheres induced 10–20 fold higher HAI responses than the control PBS formulation. A similar 10–20 fold increase in the IgG anti-influenza response was also observed (data not shown). Detectable serum IgA, fecal IgA and vaginal IgA responses were only observed in the group intranasally administered with influenza mixed with PCPP microspheres.

In a separate experimental series (data not shown), it was determined that microspheres generated by the atomization and coacervation methodologies induced similar enhancements of both the serum IgG and vaginal IgA responses to influenza. These experiments were performed on anesthetized mice given 50 µl by intranasal instillation of $2\times10^7$ microspheres adsorbed with 50 µg of influenza antigen.

Unanesthetized mice were intranasally instilled with 50 µg of split influenza antigen formulated in PBS or mixed with $1\times10^7$ empty PCPP microspheres (MS). The microspheres were generated by the spray methodology. The administration volume was 50 µl. To a control group was administered 50 µg of influenza in 50 µl PBS. FIG. 6 shows that the influenza antigen mixed with empty PCPP microsphere induced significantly higher serum IgG antibody titers at all time points (3, 6, 9, 12, 15 and 21 weeks) than the PBS influenza formulation. At week 21 post-immunization, the antigen microsphere formulation induced anti-influenza IgG titers that were approximately 8-fold higher than the antibody titers induced by the PBS formulation. Thus, the influenza mixed with microspheres demonstrated a temporally consistent significant enhancement of the serum IgG immune response. No significant serum IgA, vaginal IgA or fecal IgA antibody titers were detected after administration of either the mixed microsphere or PBS influenza formulations (data not shown).

In anesthetized mice, intranasal administration of 50 µl volumes of influenza antigens mixed with preformed microspheres enhanced the serum IgG and secretory IgA responses. The high levels of IgG response were probably induced by a deep lung immunization rather than a true intranasal immunization. In unanesthetized mice, administration of a 50 µl volume of this formulation was able to induce a very significant enhancement of the IgG immune response probably due to stimulation of immune competent tissues in the nasal passages. A 50 µl volume was used instead of 10 µl because the influenza antigen was too dilute to test in smaller volumes.

What is claimed is:

1. A method for producing an immune response in an animal comprising administering to the animal an antigen and a polyphosphazene polyelectrolyte microparticle in an amount effective to elicit an immune response, wherein the antigen has been adsorbed onto the microparticle surface.

2. The method of claim 1 wherein administering is intranasal administration.

3. The method of claim 1 wherein the antigen is selected from the group consisting of proteins, peptides, polysaccharides, glycoproteins and glycolipids.

4. The method of claim 1 wherein the antigen is selected from the group consisting of influenza proteins, hepatitis B proteins, bacterial proteins and bacterial lipopolysaccharides.

5. A composition for producing an immune response in an animal comprising a polyphosphazene microparticle and an antigen adsorbed on the microparticle surface in an amount effective to elicit an immune response.

* * * * *